United States Patent
Pujol et al.

(10) Patent No.: US 11,959,902 B2
(45) Date of Patent: Apr. 16, 2024

(54) DEVICE AND METHOD FOR DETERMINING THE HYDROCARBON-WATER CONTACT POSITION IN HYDRO-CARBON RESERVOIR

(71) Applicant: TOTALENERGIES ONETECH, Courbevoie (FR)

(72) Inventors: Magali Pujol, Pau (FR); James-Alexander Scott, Pau (FR)

(73) Assignee: TOTALENERGIES ONETECH, Courbevoie (FR)

( * ) Notice: Subject to any disclaimer, the term of this patent is extended or adjusted under 35 U.S.C. 154(b) by 0 days.

(21) Appl. No.: 18/268,672

(22) PCT Filed: Dec. 21, 2021

(86) PCT No.: PCT/EP2021/087124
§ 371 (c)(1),
(2) Date: Jun. 21, 2023

(87) PCT Pub. No.: WO2022/136453
PCT Pub. Date: Jun. 30, 2022

(65) Prior Publication Data
US 2024/0044862 A1    Feb. 8, 2024

(30) Foreign Application Priority Data
Dec. 22, 2020   (EP) .................................... 20306664

(51) Int. Cl.
G01N 33/28    (2006.01)
(52) U.S. Cl.
CPC ..... *G01N 33/2841* (2013.01); *G01N 33/2823* (2013.01)

(58) Field of Classification Search
CPC ...................... G01N 33/2841; G01N 33/2823
See application file for complete search history.

(56) References Cited

U.S. PATENT DOCUMENTS 621,169 A    3/1899  Stevens
8,061,444 B2 * 11/2011  Mullins ................ E21B 47/022
                                                  175/45

(Continued)

FOREIGN PATENT DOCUMENTS

EP    2776866 A1    9/2014
WO    2013148442 A1    10/2013
WO    2015113067 A1    7/2015

OTHER PUBLICATIONS

Barry, et al. "Noble gases solubility models of hydrocarbon charge mechanism in the 1 Sleipner Vest Gas Field." Geochimica et Cosmochimica ACTA. vol. 194. Dec. 1, 2016. pp. 291-309.

(Continued)

*Primary Examiner* — Kristina M Deherrera
*Assistant Examiner* — Jean F Morello
(74) *Attorney, Agent, or Firm* — Pearne & Gordon LLP

(57) ABSTRACT

The invention relates to a method (100) for determining a hydrocarbon-water contact position in a hydrocarbon reservoir, said method comprising the steps of:—Providing (110) at least two reservoir fluid samples collected, from connected hydrocarbon reservoir(s), at different known sampling depth values,—Measuring (120) abundance of at least one isotope of noble gas from each of the at least two reservoir fluid samples, and—Calculating (130) the hydrocarbon-water contact position in the hydrocarbon reservoir from the measured abundances and the known sampling depth values of the at least two reservoir fluid samples.

15 Claims, 6 Drawing Sheets

(56) References Cited

U.S. PATENT DOCUMENTS

2014/0250999 A1  9/2014  Lawson et al.
2014/0288853 A1  9/2014  Dreyfus et al.
2017/0242147 A1  8/2017  Ghadar et al.
2019/0257200 A1  8/2019  AbuAli et al.

OTHER PUBLICATIONS

Byrne, et al. "The use of noble gas isotopes to constrain subsurface fluid flow 1 and hydrocarbon migration in the East Texas Basin." Geochimica et Cosmochimica ACTA. vol. 268. Oct. 14, 2019. pp. 186-208.

Niculescu, et al. "Identification of Fluid Contacts by using Formation Pressure Data and Geophysical Well Logs." 19th International Multidisciplinary Scientific GeoConference SGEM 2019. Jun. 20, 2019. pp. 897-908.

International Search Report and Written Opinion for PCT/EP2021/087124, dated Apr. 4, 2022, 10 pages.

Libretexts, "2.3: Isotopic Abundance and atomic weight," https://chem.libretexts.org/Courses/University_of_Arkansas_Little_Rock/Chem_1402%3A_General_Chemistry_1_(Kattoum)/Text/2%3A_Atoms%2C_Molecules%2C_and_Ions/2.03%3A_Isotopic_Abundance_and_Atomic_Weight, pp. 1-6, Feb. 2, 2023.

\* cited by examiner

DEVICE AND METHOD FOR DETERMINING THE HYDROCARBON-WATER CONTACT POSITION IN HYDRO-CARBON RESERVOIR

FIELD OF THE INVENTION

The present invention relates to the field of exploration and appraisal of reservoirs. In particular, the invention relates to method and computer device for determining the hydrocarbon-water contact position in a hydrocarbon reservoir. More particularly, the invention provides a new method and computer device for determining the hydrocarbon-water contact depth in a hydrocarbon reservoir.

DESCRIPTION OF RELATED ART

Reservoir characterization has become increasingly important to hydrocarbon exploration. Reservoir characterization attempts to describe petroleum deposits and the nature of the rocks that contain hydrocarbons, producing detailed geological reconstructions of both its geometry and of its lithological properties. Conventional hydrocarbon exploration, development, and production practices use molecular geochemistry analysis, stable isotope analysis, and metal concentration analysis of hydrocarbon compounds in oil and gas samples. For example, it has been proposed to measure concentrations and isotopic ratios of noble gases present in a seep sample are measured and compared to a concentration of the formation water. Such a comparison allows the determination of a type, quality, hydrocarbon/water volume ratio, and/or volume of hydrocarbons associated with the subsurface accumulation is determined WO 2013/148442.

As another example, European Patent Application Publication No. EP2776866 describes measuring a clumped isotope signature from a hydrocarbon sample from a hydrocarbon seep, including determining a noble gas signature of the sample and integrating the noble gas signature and at least one or more of a clumped isotope signature or an ecology signature. The integration is then used to estimate a depth of hydrocarbons in the subsurface accumulation, a hydrocarbon/water volume ratio in the subsurface accumulation prior to escape to the surface, and a volume of the subsurface accumulation.

Such information can provide important decision support. However, such a method based on seep samples cannot be used to determine the hydrocarbon-water contact position which should be determined to locate delineation wells, plan development drilling, and forecast reserves and economics, especially when operating in high-cost areas.

Several methods have been developed to determine the hydrocarbon-water contact position. When exploring for or developing new oil and gas reservoirs, the borehole of a well may not penetrate the hydrocarbon/water contact. The position of the contact position of a hydrocarbon bearing zone can then be predicted through regression analysis using porosity $\varphi$ and water saturation $S_w$ and air permeability ka from well log and core analysis information (U.S. Pat. No. 621,169). It also has been proposed a multi-step workflow to determine oil-water contact in a dipping formation using deep directional resistivity measurements (WO2015/113067). Such methods can be completed by 2D model representing the oil-water contact with the reservoir formation above the oil-water contact. However, the use of 2D inversion is not likely to work well due to undetermined nature of the modeling (there are several models that fit the data equally well).

The above methods have had only limited success in estimating oil-water contact and are not all adapted to determine the gas-water contact. Indeed, to describe the entire reservoir, great care is required for integrating the laboratory capillary pressure data from limited core measurements alongside log data. Furthermore, if the wells in the reservoir are high above the transition zone, a small error in water saturation produces a large error in the predicted water table. Thus, prior methods are highly sensitive to certain errors that can result in large errors in the predicted hydrocarbon-water contact position.

Hence, a need exists for a new solution dedicated to determining more precisely the hydrocarbon-water contact position in a hydrocarbon reservoir, without having to use an inversion model that could bias the result and which can be applicated indifferently to an oil well or a gas well.

SUMMARY OF THE INVENTION

It is an object of the present invention to provide a method for determining the hydrocarbon-water contact position in an oil and/or gas well preferably from abundance values of isotopes of noble gases generated from at least two reservoir samples collected at known depth values in only one exploratory well.

The following sets forth a simplified summary of selected aspects, embodiments and examples of the present invention for the purpose of providing a basic understanding of the invention. However, the summary does not constitute an extensive overview of all the aspects, embodiments, and examples of the invention. The sole purpose of the summary is to present selected aspects, embodiments, and examples of the invention in a concise form as an introduction to the more detailed description of the aspects, embodiments and examples of the invention that follow the summary.

The invention aims to overcome the disadvantages of the prior art. In particular, the invention proposes a method to determine the hydrocarbon-water contact position based on abundance values of isotopes of noble gases, said method allowing to directly connect abundance values of isotopes of noble gases and depth of collection to hydrocarbon-water contact position. Advantageously, such a method based on reservoir samples collected at known depth values allows to determine hydrocarbon-water contact position of several reservoir with only one exploratory well.

The invention also proposes a computer device configured to determine the hydrocarbon-water contact position. Advantageously, a solution according to the invention can produce reliable values from only one exploratory well going through several reservoirs.

Hence, according to an aspect of the present invention, it is provided a method for determining a hydrocarbon-water contact position in connected hydrocarbon reservoir(s), said method comprising the steps of:
  Providing at least two reservoir fluid samples collected, from connected hydrocarbon reservoir(s), at different known sampling depth values,
  Measuring abundance of at least one isotope of noble gas from each of the at least two reservoir fluid samples, and
  Calculating the hydrocarbon-water contact position in the hydrocarbon reservoir from the measured abundances and the known sampling depth values of the at least two reservoir fluid samples.

Instead of using classical well log information, a method according to the invention is based on isotopic abundance of noble gases in hydrocarbon reservoir as a function of a hydrocarbon-water contact distance. Advantageously, this method can be used to determine a relationship between abundance and depth to determine a hydrocarbon-water contact position. Such method can be done with data coming from only one exploration well or multiple and do not require the implementation of complex modeling that can be subject to bias.

According to other optional features of the method, it can optionally include one or more of the following characteristics alone or in combination:

- the hydrocarbon-water contact position is an oil-water contact position or a gas-water contact position. In particular, the present invention can be applied to determine an oil-water position or a gas-water whereas known techniques are not as versatile are only effective on one or other of these contact positions.
- the at least two reservoir fluid samples were collected at known depth varying of at least ten meters. This allows the method to have better accuracy and precision in determining the hydrocarbon-water contact position.
- the at least two reservoir fluid samples were collected from one same connected reservoir unit. Alternatively, the at least two reservoir fluid samples were collected from several different connected reservoirs units. When hydrocarbon reservoirs are connected to a same aquifer, reservoir fluid can be sampled in different reservoir, hence this facilitates the implementation of the method in particular when the reservoirs heights are low or when the number of samples must be reduced. Alternatively, a single well, crossing several reservoirs which are not connected to the same aquifer, can be used to determine the hydrocarbon-water contact position in any of the reservoirs crossed. Hence, a method according to the invention is highly versatile regarding the position of the collected samples.
- the at least two reservoir fluid samples are downhole samples.
- the at least two reservoir fluid samples were collected in one or more wells from the same reservoir unit or connected reservoir units. Hydrocarbon-water contact position will be significantly more accurate if reservoir fluid samples are collected in the well(s) and not at the well head. More preferably, the at least two reservoir fluid samples are downhole samples.
- Moreover, the method can be applied for several disconnected reservoirs and at least two reservoir fluid samples are provided for each disconnected reservoir.
- wherein reservoir fluid samples have been collected by a formation tester or a drill stem test directly from the hydrocarbon reservoir at reservoir pressure and temperature conditions. This allows the method to have better accuracy and precision in determining the hydrocarbon-water contact position.
- it comprises a step of collecting the at least two reservoir fluid samples by a formation tester at reservoir pressure and temperature conditions of the connected hydrocarbon reservoir. This allows the method to have better accuracy and precision in determining the hydrocarbon-water contact position.
- it comprises a step of bringing reservoirs fluid samples to the surface and transferring them into PVT sampling bottles. This allows the method to have better accuracy and precision in determining the hydrocarbon-water contact position.
- it comprises a step of subsampling noble gas from the at least two reservoir fluid samples. Preferably, the subsampling of noble gas is done in controlled conditions of pressure and temperature. This allows the method to have better accuracy and precision in determining the hydrocarbon-water contact position.
- the step of measuring abundance of at least one isotope of noble gas comprises the analysis, preferably by mass spectrometry, of at least one noble gas isotope selected from: $^{3}$He, $^{4}$He, $^{20}$Ne, $^{21}$Ne, $^{22}$Ne, $^{36}$Ar, $^{38}$Ar, $^{40}$Ar, $^{78}$Kr, $^{80}$Kr, $^{82}$Kr, $^{83}$Kr, $^{84}$Kr, $^{88}$Kr, and $^{124}$Xe, $^{126}$Xe, $^{128}$Xe, $^{129}$Xe, $^{130}$Xe, $^{131}$Xe, $^{132}$Xe, $^{133}$Xe, $^{134}$Xe.
- a step of evaluating contamination or fractionation of noble gas in the at least two reservoirs fluid samples. Preferably, when contamination or fractionation is detected, the sample is discarded.
- the step of calculating hydrocarbon-water contact position from the measured abundances and known depth values of collection comprises the use of predetermined abundance values of isotopes of noble gases. Indeed, calculation method, for example when using supervised learning model or other regression methods, can benefit from predetermined abundance values. Preferably, the step of calculating hydrocarbon-water contact position comprises the use of predetermined abundance values of at least one or at least two isotopes of noble gases.

Other implementations of this aspect include computer systems, apparatuses and corresponding computer a recorded on one or more computer storage devices, each configured to perform at least some of the actions of a method according to the invention. In particular, a system of one or more computers can be configured to perform specific operations or actions, in particular a method according to the invention, by means of the installation of software, firmware, hardware or a combination software, firmware, or hardware installed on the system. In addition, one or more computer programs can be configured to perform particular operations or actions through instructions which, when executed by a data processing apparatus, compel the apparatus to perform the actions.

According to another aspect of the present invention, it is provided a computer device for determining a hydrocarbon-water contact position in a hydrocarbon reservoir, said computer device comprising:

A communication interface configured to acquire:
  Measured abundance value of at least one isotope of noble gas from each of at least two reservoir fluid samples from the hydrocarbon reservoir, and
  Depth of collection values of the at least two reservoir fluid samples in the hydrocarbon reservoir;
A processor configured to calculate hydrocarbon-water contact position in the hydrocarbon reservoir, from the measured abundance values and known depth values of the at least two reservoir fluid samples.

According to another aspect of the present invention, it is provided a non-transitory computer readable medium storing executable instructions which, when executed by a processor of a computer device, implements a method according to the invention.

BRIEF DESCRIPTION OF THE DRAWINGS

The foregoing and other objects, features and advantages of the present invention will become more apparent from the following detailed description when taken in conjunction with the accompanying drawings in which.

Figure 1:
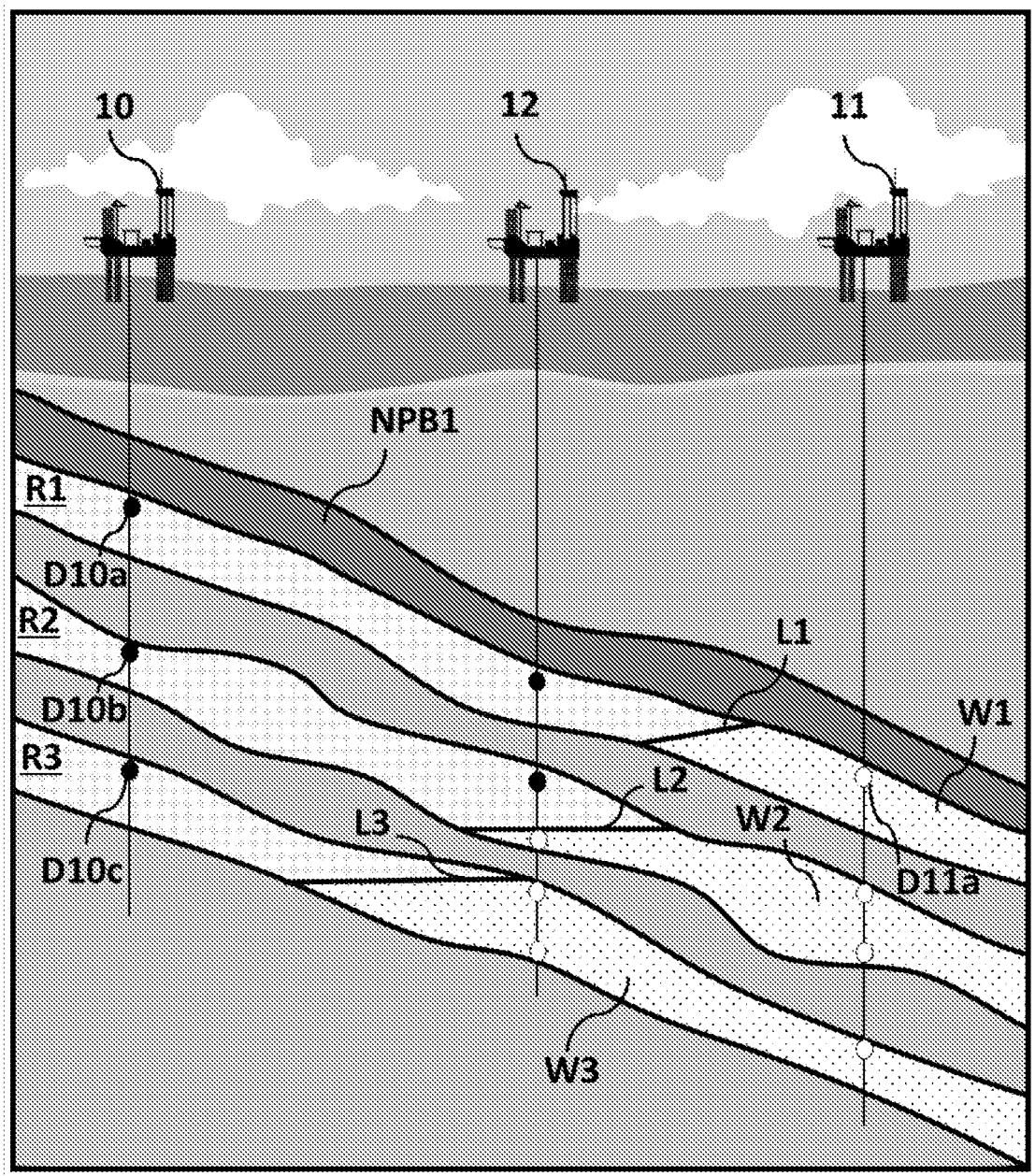
FIG. 1 is an illustration showing the determination of a hydrocarbon-water contact position in several hydrocarbon reservoirs by a drilling platform according to a known solution.

Several aspects of the present invention are disclosed with reference to flow diagrams and/or block diagrams of methods, devices and computer program products according to embodiments of the invention.

On the figures, the flow diagrams and/or block diagrams show the architecture, the functionality and possible implementation of devices or systems or methods and computer program products, according to several embodiments of the invention.

For this purpose, each box in the flow diagrams or block diagrams may represent a system, a device, a module or code which comprises several executable instructions for implementing the specified logical function(s). In some implementations, the functions associated with the box may appear in a different order than indicated in the figures. For example, two boxes successively shown, may be executed substantially simultaneously, or boxes may sometimes be executed in the reverse order, depending on the functionality involved.

Each box of flow diagrams or block diagrams and combinations of boxes in flow diagrams or block diagrams, may be implemented by special systems that perform the specified functions or actions or perform combinations of special equipment and computer instructions.

Thus, as will be appreciated by those skilled in the art, aspects of the present invention can be realized as a device, system, method or product of computer program. Accordingly, aspects of the present invention may take the form of a fully hardware embodiment, a fully software embodiment (including firmware, resident software, microcode, etc.) or a mode of particular implementation such as a "circuit", "module" or "system". In addition, aspects of the present invention may take the form of a computer program product embedded in one or more computer readable media having a computer readable program code embedded therein.

Any combination of one or more computer-readable media can be used. In the context of this document, a computer readable medium can be any tangible medium which can contain or store a program to be used by or in connection with an instruction execution system, apparatus or device. A computer readable medium may be, for example, but not limited to, an electronic, magnetic, optical, electromagnetic, infrared or semiconductor system, apparatus or device, or any suitable combination of the above. More specific examples (a non-exhaustive list) of computer-readable storage media would include: a hard drive, random access memory (RAM).

Computer program code for performing operations for aspects of the present invention can be written in any combination of one or more programming languages, including an object oriented programming language such as Java, C++ or similar, the "C" programming language or similar programming languages, a scripting language such as Perl, or similar languages, and/or functional languages such as Meta Language. Program code can run entirely on a user's computer, partially on a user's computer and partially on a remote computer, or entirely on the remote computer or server. In the latter scenario, the remote computer can be connected to a user's computer over any type of network, including a local area network (LAN) or a wide area network (WAN).

These computer program instructions can be stored on a computer-readable medium capable of directing a computer device (e.g. computer, server, etc.), so that the instructions stored in the computer-readable medium produce a computer device configured to implement the invention.

DETAILED DESCRIPTION

A description of example embodiments of the invention follows.

In the following description, "noble gases" refers to a series of chemically inert elements that exhibit similar properties. The noble gases are a group of chemically inert, or conservative, gases which have a low natural abundance in crustal systems. Various physical processes have resulted in different pools of noble gases (the mantle, atmospheric and crustal pools) becoming distinct in their isotopic composition and relative elemental abundances. The five noble gases of particular interest in the present invention are helium (He), neon (Ne), argon (Ar), krypton (Kr) and xenon (Xe).

As used herein the term "isotope" refers to one of two or more atoms with the same atomic number but with different numbers of neutrons. For example, argon can be present as one of three stable isotopes: $^{40}Ar$, which has 18 protons and 22 neutrons, $^{38}Ar$, which has 18 protons and 20 neutrons, and $^{36}Ar$, which has 18 protons and 18 neutrons.

As used herein the term "aquifer" refers to an area where water is occurring in the porous media within the accumulation or immediately below but in contact with the hydrocarbon accumulation. This water occurring in the porous media may derive from recharge of surface waters such as rainwater or seawater that then migrates through permeable rock within the subsurface, and/or water trapped in the sediment during burial and remaining in place.

As used herein "hydrocarbons" are generally defined as molecules formed primarily of carbon and hydrogen atoms such as oil and natural gas. Hydrocarbons may also include other elements or compounds, such as, but not limited to, halogens, metallic elements, nitrogen, oxygen, and sulfur. Hydrocarbons derived from a hydrocarbon reservoir may include, but are not limited to, petroleum, kerogen, bitumen, pyrobitumen, asphaltenes, tars, oils, natural gas, or combinations thereof.

As used herein, the term "reservoir" or "petroleum reservoir" can refers to a subsurface group of sedimentary, metamorphic or igneous rocks capable of storing an accumulation of hydrocarbons. This is commonly a porous sandstone or limestone but not exclusively. Connected hydrocarbon reservoir(s) can for example refer to one or several a subsurface group of hydrocarbon bearing rock, containing porosity, permeability, with sufficient hydrocarbon accumulation and a sealing mechanism to form a reserve or accumulation. Typically, hydrocarbon reservoir is an accumulation from which commercial flows of hydrocarbon can be produced.

As used herein, "hydrocarbon exploration" refers to any activity associated with determining the location of hydrocarbons in subsurface regions. Hydrocarbon exploration normally refers to any activity conducted to obtain measurements through acquisition of measured data associated with the subsurface formation and the associated modeling of the data to identify potential locations of hydrocarbon accumulations. Accordingly, hydrocarbon exploration includes acquiring measurement data, modeling of the measurement data to form subsurface models, and determining the likely locations for hydrocarbon reservoirs within the subsurface.

"Hydrocarbon-water contact position" (HWC) is an expression used to describe a bounding surface in a reservoir above which predominantly hydrocarbon (i.e. oil or gas) occurs and below which predominantly water occurs. The position of the hydrocarbon-water contact can for example be expressed as depth or as a distance from surface. When a 2D or 3D map is available, the hydrocarbon-water contact position can also correspond to a location on the map.

By "process", "compute", "determine", "display", "extract", "compare" or more broadly "executable operation" is meant, within the meaning of the invention, an action performed by a computer device or a processor unless the context indicates otherwise. In this regard, the operations relate to actions and/or processes of a data processing system, for example a computer system or an electronic computing device, which manipulates and transforms the data represented as physical (electronic) quantities in the memories of the computer system or other devices for storing, transmitting or displaying information. In particular, calculation operations are carried out by the processor of the device, the produced data are entered in a corresponding field in a data memory and this field or these fields can be returned to a user for example through a Human Machine Interface formatting such data. These operations may be based on applications or software.

The terms or expressions "application", "software", "program code", and "executable code" mean any expression, code or notation, of a set of instructions intended to cause a data processing to perform a particular function directly or indirectly (for example after a conversion operation into another code). Exemplary program codes may include, but are not limited to, a subprogram, a function, an executable application, a source code, an object code, a library and/or any other sequence of instructions designed for being performed on a computer system.

By "processor" is meant, within the meaning of the invention, at least one hardware circuit configured to perform operations according to instructions contained in a code. The hardware circuit may be an integrated circuit. Examples of a processor include, but are not limited to, a central processing unit, a graphics processor, an application-specific integrated circuit ("ASIC" according to Anglo-Saxon terminology), and a programmable logic circuit. A single processor or several other units may be used to implement the invention.

By "coupled" is meant, within the meaning of the invention, connected, directly or indirectly, with one or more intermediate elements. Two elements may be coupled mechanically, electrically or linked by a communication channel.

The expression "human-machine interface", within the meaning of the invention, corresponds to any element allowing a human being to communicate with a computer, in particular and without that list being exhaustive, a keyboard and means allowing in response to the commands entered on the keyboard to perform displays and optionally to select with the mouse or a touchpad items displayed on the screen. Another embodiment is a touch screen for selecting directly on the screen the elements touched by the finger or an object and optionally with the possibility of displaying a virtual keyboard.

By "computer device", it should be understood any device comprising a processing unit or a processor, for example in the form of a microcontroller cooperating with a data memory, possibly a program memory, said memories possibly being dissociated. The processing unit cooperates with said memories by means of internal communication bus.

The term "substantially" as used herein refers to a majority of, or mostly, as in at least 50%, 60%, 70%, 80%, 90%, 95%, 96%, 97%, 98%, 99%, 99.5%, 99.9%, 99.99%, or at least 99.999% or more.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements.

In the following description, "ensemble prediction method" means a type of machine learning method that uses a series of learners to learn and uses some rules to integrate the learning results so as to achieve better learning effects than a single learner. The main idea of ensemble learning is to first generate a number of learners according to certain rules and then combine them by some integration strategies, and eventually output the final results by comprehensive judgment. Briefly, what ensemble learning does is to integrate multiple weak learners into one strong learner. Such ensemble prediction method can for example be selected from: Random Forest (RF, Breiman, 1996; 2001) and Extreme Gradient Boosting (XGBOOST, Chen and Guestrin, 2016). An ensemble prediction method is used to produce an ensemble prediction model.

Additionally, it should be understood that references to "one embodiment" or "an embodiment" of the present disclosure are not intended to be interpreted as excluding the existence of additional embodiments that also incorporate the recited features.

As mentioned, determination of the hydrocarbon-water contact position is of utmost importance for the reservoir characterization and, during exploration and reservoir characterization, appraisal wells are usually drilled in order to determine this hydrocarbon-water contact position for each hydrocarbon reservoir.

To answer these issues, the inventors developed solutions dedicated to the predicting the position of the hydrocarbon-water contact, OWC for "oil-water contact" or GWC for "gas-water contact", using isotopes of noble gases and preferably from data coming from only one exploration well, but not exclusively.

All fluids have a noble gas fingerprint, controlled by the source of isotopes of noble gases and the fluid history. Those gas fingerprints are based on noble gas inherited from source rock(s), secondarily modified by transport and residence time in reservoir.

The use of noble gas has already been proposed in the field of exploration and appreciation of reservoirs as they are affected by physical processes (radioactive decay; transport; mixing; phase changes . . . ) but not by any chemical or biological process. However, their use has never been proposed, to the best of inventors' knowledge, to determine a hydrocarbon-water contact position.

Inventors developed solutions to determine a hydrocarbon-water contact position in a hydrocarbon reservoir based on abundance of at least one isotope of noble gas in at least two reservoir fluid samples collected at known depth. Such method allows a rapid and simple estimation of hydrocarbon-water contact position from one or several exploration wells.

Hence, according to a first aspect, the invention relates to a method 100 for determining a hydrocarbon-water contact position in a hydrocarbon reservoir.

As shown in FIG. 1, the determination of a hydrocarbon-water contact position in a hydrocarbon reservoir is usually done by drilling a first exploration well to be followed by appraisal wells. In FIG. 1, the exploration well 10 confirmed occurrences of hydrocarbons in the reservoirs R1, R2, R3 through samples, represented as black point, collected at different known depth D10a D10b, D10c. The exploratory well encountered only hydrocarbons and can only be used with difficulty to estimate the hydrocarbon-water contact position by traditional methods. However, the first appraisal well 11 encountered only water. Thus, it was only able to confirm presence of water through samples (represented as white point) collected at different known depth D11a and determine a water up to (WUT) value. It was of no use for determination of a hydrocarbon-water contact position. Only the second appraisal well 12 allows an estimation of the hydrocarbon-water contact position but just for the second hydrocarbon reservoir R2. Hence, in this example, the determination of incomplete data on hydrocarbon-water contact position necessitate one exploration well 10 and two appraisal wells 11, 12 which is a costly process at this exploration stage.

An example of an HWC represented by references L1, L2, L3 in a reservoir R1, R2, R3 is shown in FIG. 1. In an oil or gas field, hydrocarbons migrate into rocks and can be trapped if there is a non-permeable barrier NPB1 to prevent upward escape. The hydrocarbons are lighter than water W1, W2, W3, so the gas and oil form a bubble at a high end of a "trap" formed by the non-permeable barrier NPB1. Although oil and water are immiscible, the contact between oil and water may be a transition zone and there may be irreducible water adsorbed by the grains in the rock and immovable oil that cannot be produced.

Figure 2:
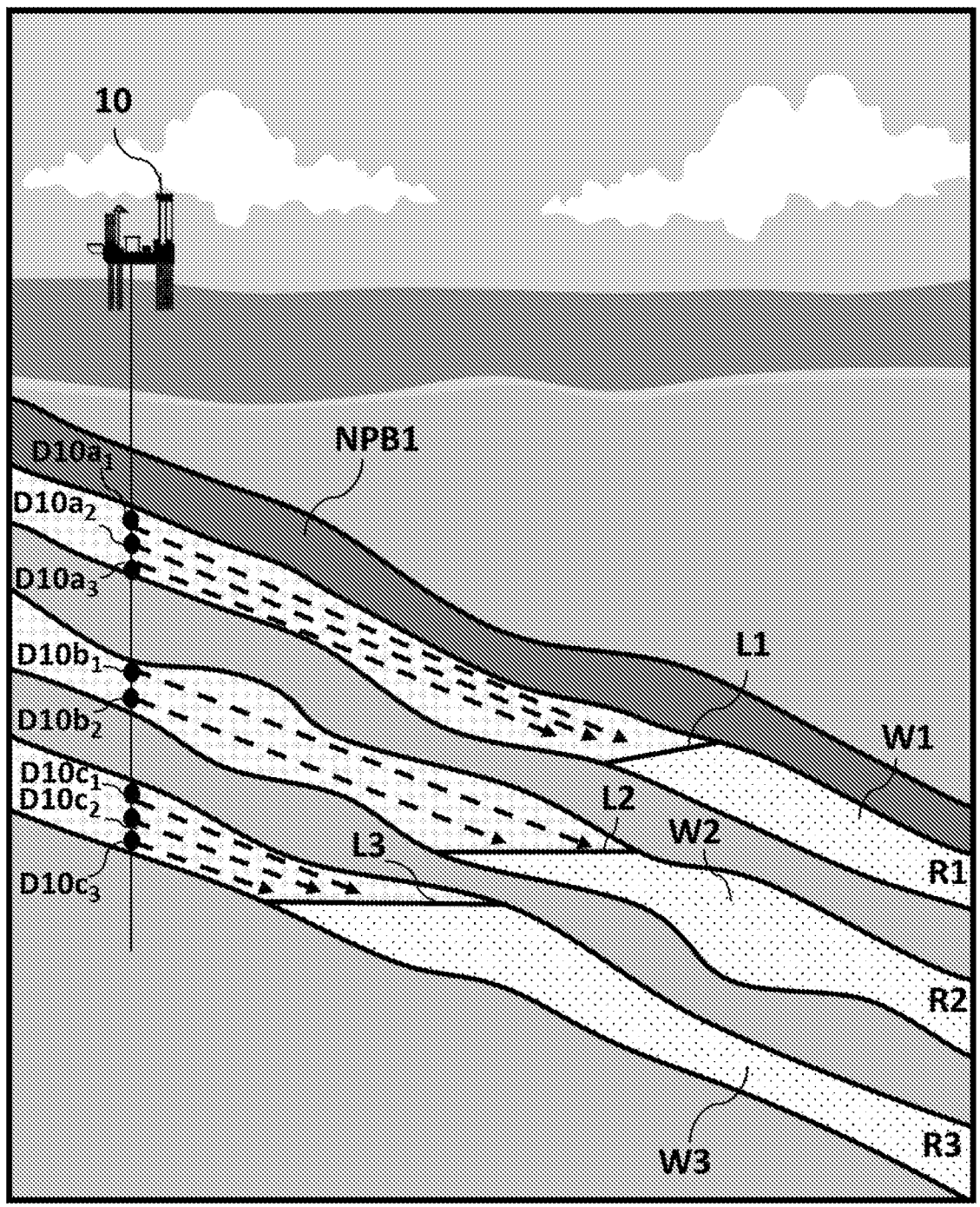
FIG. 2 is an illustration showing the determination of a hydrocarbon-water contact position in several hydrocarbon reservoirs by a drilling platform according to the invention.

As illustrated in the FIG. 2, a solution according to the invention allows the determination of a hydrocarbon-water contact position L1, L2, L3 with only one exploration well 10. Indeed, the solution is based on at least two reservoirs fluid samples collected at different known depth value represented by references $D10a_1$, $D10a_2$, $D10a_3$ for the reservoir R1, $D10b_1$, $D10b_2$ for the reservoir R2, and $D10c_1$, $D10c_2$, $D10c_3$ for the reservoir R3. The abundance of at least one isotope of noble gas from each of the at least two reservoirs fluid samples, is then used with the known depth values to calculate a hydrocarbon-water contact position in the hydrocarbon reservoir.

As already stated, a method according to the invention allow the determination of a hydrocarbon-water contact position. Such hydrocarbon-water contact position can for example be expressed in depth or in distance from the well or from collecting points. Preferably, the hydrocarbon-water contact position refers to the hydrocarbon-water contact depth in hydrocarbon reservoir.

In particular, the hydrocarbon-water contact depth is an oil-water contact depth or a gas-water contact depth.

As illustrated in figures, the determination of the hydrocarbon-water contact depth can be applied for several reservoirs R1, R2, R3. Such reservoirs can be connected (FIG. 3) or not connected (FIGS. 1 and 2).

Figure 3:
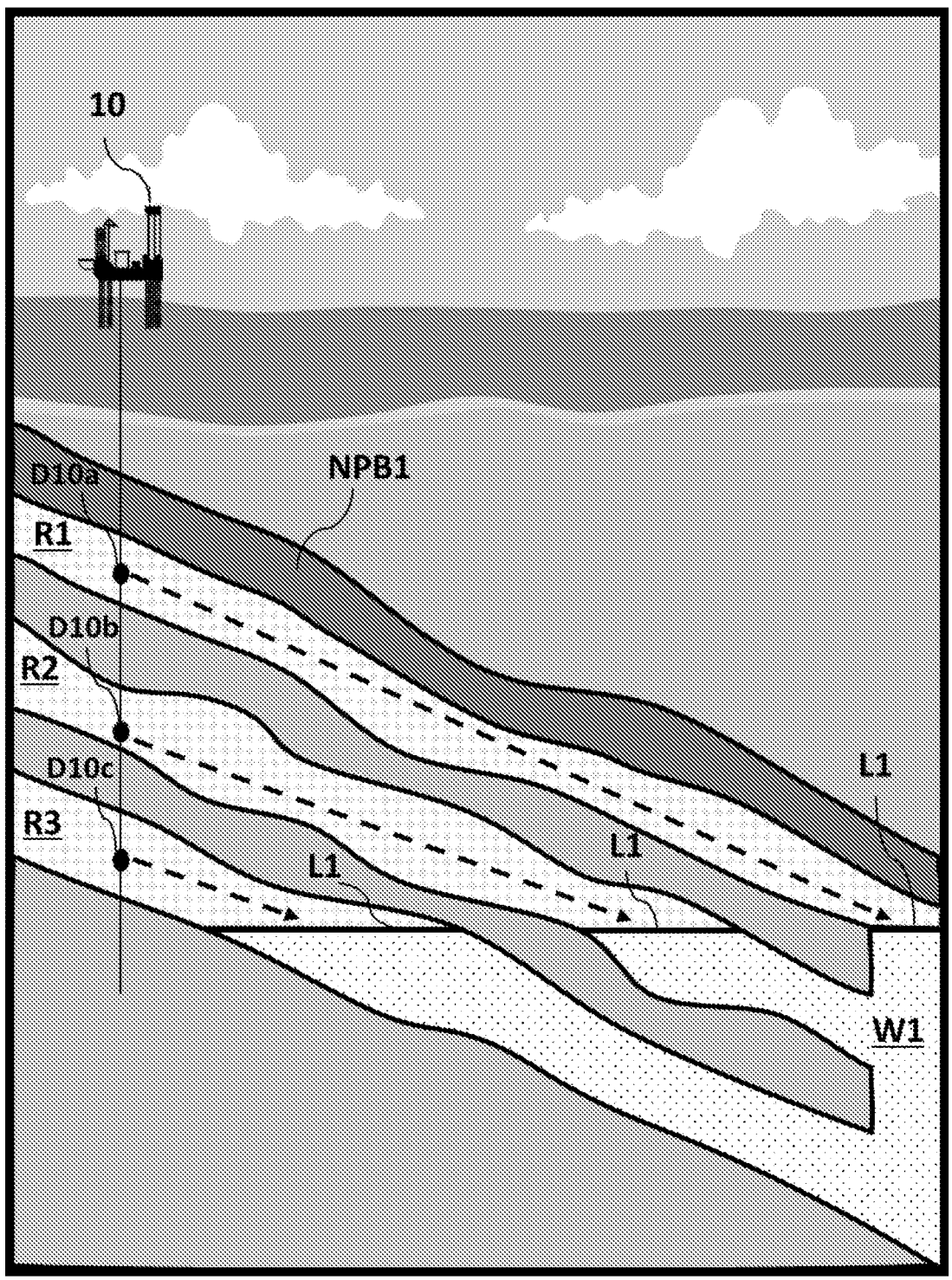
FIG. 3 is an illustration showing the determination of a hydrocarbon-water contact position in connected hydrocarbon reservoirs by a drilling platform according to the invention.

Referring to FIG. 3, when the reservoirs R1, R2, R3 are connected, they share a same hydrocarbon-water contact position L1. Hence, the at least two reservoirs fluid samples can be collected at different known depth value D10a, D10b, D10c of different reservoirs R1, R2, R3.

Preferably, the determination of the hydrocarbon-water contact depth is applied for several reservoirs unconnected and thus with varying hydrocarbon-water contact position.

Figure 4:
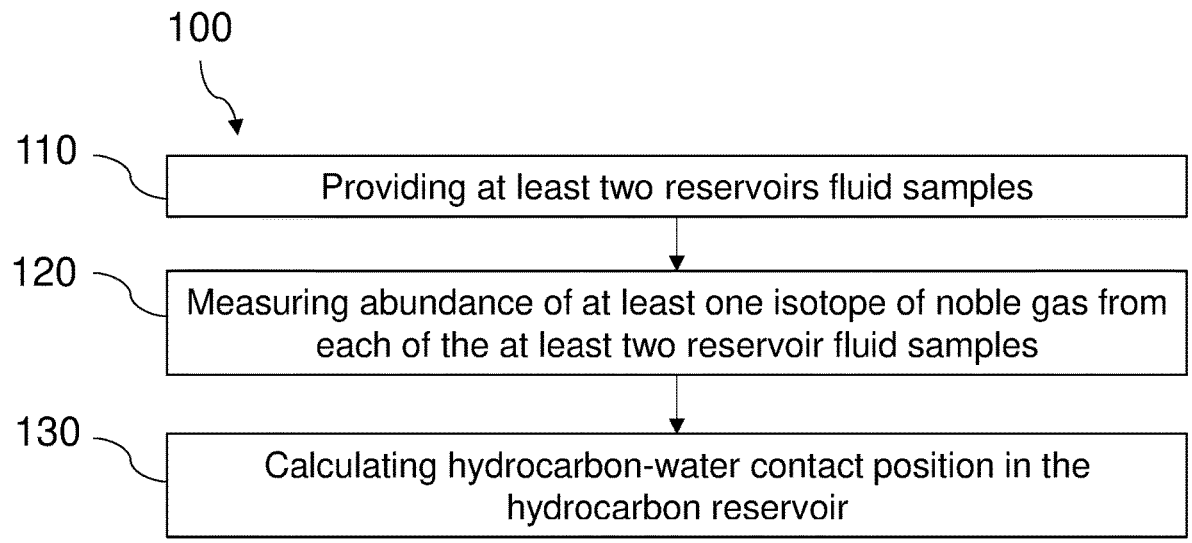
FIG. 4 is a schematic view showing a process flow diagram of a method according to an embodiment of the invention.

As illustrated in, FIG. 4, a method 100 for determining a hydrocarbon-water contact position in connected hydrocarbon reservoir(s) according to the invention comprises in particular the steps of: providing 110 at least two reservoirs fluid samples, measuring 120 the abundance of at least one isotope of noble gas from each of the at least two reservoirs fluid samples, and calculating 130 hydrocarbon-water contact distance or preferably depth in the hydrocarbon reservoir from the measured abundances and known depth of sampling values of the at least two reservoirs fluid samples.

A First Step of the Method According to the Invention can be a Step of Providing 110 at Least Two Reservoir Fluid Samples.

Such reservoirs fluid samples are preferably collected from a hydrocarbon reservoir or from two hydrocarbon reservoirs connected with a single aquifer, such hydrocarbon reservoirs being also called connected hydrocarbon reservoirs. Such reservoirs fluid samples are preferably collected from a single hydrocarbon reservoir. In particular, the at least two reservoirs fluid samples were collected from the same reservoir. Hence, the at least two reservoirs fluid samples were collected from varying depth of a same reservoir or from varying depth of connected same reservoirs.

Alternatively, reservoirs fluid samples can be collected from two connected hydrocarbon reservoirs at different known depth value. Usually, the connected hydrocarbon reservoirs are connected with a single aquifer, such as represented by the reference W1 in FIG. 3. Hence reservoir fluid samples from, at least two or each connected reservoir are sufficient to calculate the hydrocarbon-water contact position.

Advantageously and unlike many prior art methods, the reservoirs fluid samples are collected directly at a drilling depth and not from the well head. Previous methods which were based on surface seep samples did not allow the method according to the invention to be implemented. Indeed, such surface seep samples are usually contaminated by surface atmosphere and secondly are difficult to associate with a depth value.

Hence, preferably, the at least two reservoir fluid samples used in the present invention were collected in the well.

Moreover, as part of the present invention, knowing the depth of collection (e.g. depth or distance from the surface) is of utmost importance. Hence, according to the invention, the at least two reservoirs fluid samples were collected at different known depth value. The depth value can correspond to the distance drilled of to the depth from the surface.

Advantageously, the at least two reservoirs fluid samples used in a method according to the invention were collected at known depth varying of at least ten meters. In particular, the at least two reservoir fluid samples were collected from different locations, said different location being separated by a distance of at least ten meters. Indeed, with at least ten meters in depth or in distance between the collection locations of the at least two reservoirs fluid samples the calculated hydrocarbon-water contact position is the more accurate. In the same way, the at least two reservoirs fluid samples used in a method according to the invention can be collected at known depth or at collection location distance varying of at least 20 meters preferably at least 50 meters, more preferably at least 100 meters, even more preferably at least 200 meters, for example at least 500 meters. Indeed, the more distance between two reservoir samples the more accurate is the calculated hydrocarbon-water contact position. However, as the method according to the invention is particularly suited for connected hydrocarbon reservoir(s), the at least two reservoirs fluid samples used in a method according to the invention can be collected at known depth or at collection location distance varying of at most 800 meters preferably at most 500 meters, more preferably at most 200 meters, even more preferably at most 100 meters, for example at most 50 meters.

There are many methods for collecting samples from wells at known depths. In particular, the at least two reservoirs fluid samples used in a method according to the invention were collected by a formation tester e.g. RFT (for "Repeat Formation Tester"), MDT (for "modular formation dynamic tester"), TLC (for 'Tubing Logging Convey'), WFT (for "Wireline Formation Tester"), DST (for "Drill Stem Test") directly from a reservoir formation at reservoir pressure and temperature conditions. Preferably, the at least two reservoirs fluid samples used in a method according to the invention were collected by a formation tester selected from: RFT, MDT and WFT.

Such a method of collection can advantageously be done concomitantly with the drilling process.

Figure 5:
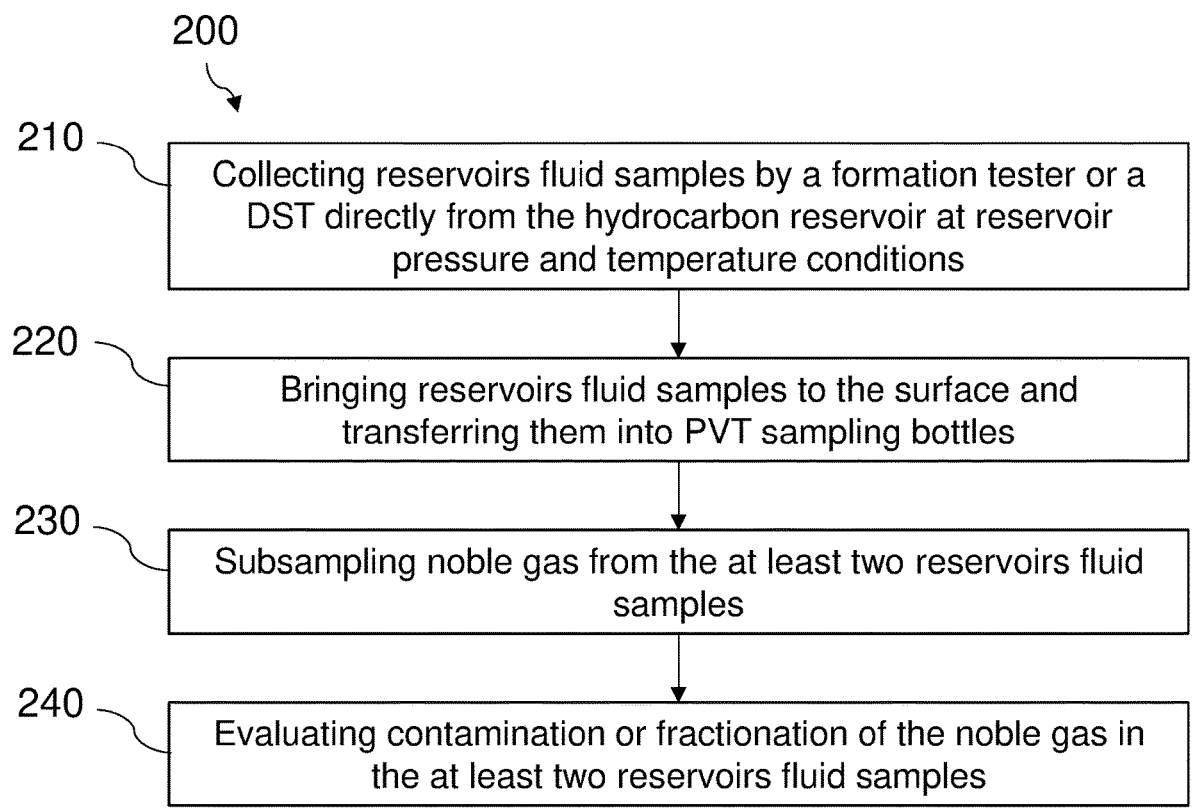
FIG. 5 is a schematic view showing a process flow diagram related to the collection of reservoir fluid samples of a method according to the invention.

As illustrated in the FIG. 5, the method according to the invention can also comprise steps related to the collection 200 of the reservoir fluid samples.

Hence, a method according to the invention can comprise collecting 210 reservoirs fluid samples; Bringing 220 reservoirs fluid samples to the surface; Subsampling 230 noble gases from the at least two reservoirs fluid samples; Evaluating 240 contamination or fractionation of the noble gas.

The method according to the invention can be based on data generated from a well drilled to subsurface reservoir having hydrocarbons. The drilling of the well may be performed using commonly used techniques. Then, samples may be obtained preferably concurrent with the drilling of the well or subsequent to the drilling of the well.

The collection method begins at block 210. In block 210, samples of hydrocarbons are collected at different depth. In particular, the fluid samples are collected directly from the hydrocarbon reservoir at reservoir pressure and temperature conditions. This can be done for example using a formation tester.

Preferably, the fluid samples are collected from different depth with at least a ten meters distance interval between each sampling, for example at least 20 meters preferably at least meters, more preferably at least 100 meters, even more preferably at least 200 meters, for example at least 500 meters. These samples are preferably kept in PVT (for "Pressure, Volume, Temperature") conditions similar, more preferably substantially identical to the PVT conditions of the sampling location. Such embodiment will allow a better accuracy for the hydrocarbon-water contact position determination. Unlike the prior art methods, the gas sample is not collected from mud circulating in the well bore as the accuracy of the measured abundances will not be sufficient to properly determine the hydrocarbon-water contact position.

Hence, advantageously, a method according to the invention comprises a step of collecting 210 reservoirs fluid samples by a formation tester directly from the hydrocarbon reservoir at reservoir pressure and temperature conditions. Preferably coupled with a significant flushing of the jars, this will limit mud contamination, air pollution issue and fractionation. In particular, reservoir fluid samples can be collected by formation tester techniques, such as drill stem tests (DST), repeat formation tester (RFT), modular dynamic testing (MDT), Tubing Logging Convey (TLC), or Wireline Formation Tester (WFT), such formation testers being used directly from the reservoir formation at reservoir pressure and temperature conditions.

Once the samples are obtained, the formation tester, comprising the reservoirs fluid samples are brought 220 to the surface. The reservoirs fluid samples can then be transferred to transportable PVT bottles. Those transportable bottles will limit air pollution during transport/storage and can be used to transport the reservoirs fluid samples to a laboratory in charge of measuring isotopes of noble gases abundances.

Measurement of the abundance of each noble gas isotope can be conducted following standard extraction techniques using mass spectrometry.

Several methods have been proposed for measurement of abundance value of each noble gas isotope. Moreover, recent studies reconstructed the noble gas composition of the oil phase from casing gas measurements using broad assumptions about gas solubility in oil (e.g., Barry et al., 2018a, Tracing enhanced oil recovery signatures in casing gases using noble gases. Earth Planet. Sci. Lett. 496, 57-67; Barry et al., 2018b, Noble gases in deep-water oils of the U.S. Gulf of Mexico. Geochem. Geophys. Geosyst. 19(11), 4218-4235). Noble gases measurement requires a gas mass spectrometer combined with an extraction/purification line. For good quality results, the role of the purification line is to remove all molecules that are not a noble gas. To do so mainly chemical traps are used. Therefore, having fewer molecules in the sample decreases the sample purification time and efficiency. Moreover, the purification line (outside chemical traps) is regularly baked and pumped under high vacuum to remove residual pollution.

However, preferably, measurement of abundance value of each noble gas isotope is preceded by a step of subsampling 230 noble gas from the at least two reservoirs fluid samples. In particular, noble gas including their isotopes are subsampled from pressurized reservoir fluid.

Such subsampling method can comprise the analysis of the composition of the gas that has degassed a monophasic fluid (outlined in Holland and Gilfillan, 2013, Application of noble gases to the viability of $CO_2$ storage. In *The noble gases as geochemical tracers* (pp. 177-223). Springer, Berlin, Heidelberg & Ballentine et al., 1996, A Magnus opus: Helium, neon, and argon isotopes in a North Sea oilfield. *Geochimica* et *Cosmochimica Acta*, 60(5), 831-849). However, there are two main issues with these methods, 1) Many studies wrongly assume that when a gas ex solves from a fluid all of the noble gases will partition into the gas phase and 2) the PVT conditions during sample collection are poorly constrained (Tyne et al., 2019, Tracing the Fate of Injected CO2 using Noble Gas Isotopes. In *AGU Fall Meeting* 2019. AGU). The results obtained are often from highly fractionated samples. In addition to the flawed sampling method, the equation used for recalculating the original composition is over simplified (Ballentine et al., 1996).

Hence, preferably, the subsampling can comprise the use of a system or a method allowing the preparation of a gaseous subsample from a monophasic fluid wherein the pressure, volume and temperature conditions are fully controlled when the monophasic fluid is transformed in a diphasic fluid (i.e., bubble point pressure, PV curve). By knowing the precise condition when the bubble point occurred, it is possible to accurately calculate the original noble gas signature of the monophasic fluid. In particular, monophasic liquid samples, a split of the sample in diphasic domain under equilibrium and under controlled conditions of pressure and temperature enable an analyze dedicated to the gas phase to rebuild the initial fluid composition. Preferably, the subsampling comprises the preparation of representative samples of the monophasic fluid which are not fractionated. All subsampling steps are well constrained, and the conditions of sampling are controlled and recorded. This allows a true determination of chemical content such as noble gas fingerprint of a monophasic fluid.

Measurement of the abundance of each noble gas isotope can also be preceded by an evaluation 240 of the contamination or the fractionation of the noble gas. In particular, noble gases can undergo quality control process, to check that samples are representative of the fluid samples with no evidence of contamination or fractionation. When evidence of contamination or fractionation are found, the sample is discarded.

Back to FIG. 4, the invention also comprises a step of measuring 120 the abundance of at least one isotope of noble gas from each of the at least two reservoir fluid samples. The step of measuring 120 can be done for at least two isotopes of noble gases or more than two isotopes of noble gases, for example for at least three, preferably at least four isotopes of noble gases. Similarly, step of measuring 120 can be done for more than two reservoir fluid samples, for example for at least three, preferably at least four reservoir fluid samples.

Noble gas abundances are generally measured on a mass spectrometry. In particular, noble gas abundances can be measured by several mass spectrometry methods such as: gas chromatography-mass spectrometry (GC/MS), GC/MS/MS, inductively coupled plasma mass spectrometry (ICP-MS) or more specifically isotope ratio-mass spectrometry.

In particular, this step of measuring 120 the abundance of noble gas isotope comprises the measurement of the abundance, preferably by mass spectrometry, of at least one isotope of noble gas selected from: $^{3}$He, $^{4}$He, $^{20}$Ne, $^{21}$Ne, $^{22}$Ne, $^{36}$Ar, $^{38}$Ar, $^{40}$Ar, $^{78}$Kr, $^{80}$Kr, $^{82}$Kr, $^{83}$Kr, $^{84}$Kr, $^{88}$Kr, and $^{124}$Xe, $^{126}$Xe, $^{128}$Xe, $^{129}$Xe, $^{130}$Xe, $^{131}$Xe, $^{132}$Xe, $^{133}$Xe, $^{134}$Xe. In particular, the present invention can comprise the measurement of the abundance of at least three isotopes of noble gases, preferably of at least four isotopes of noble gases.

The noble gas isotopes whose abundances are measured can correspond to isotopes of one noble gas, such as $^{3}$He, $^{4}$He; $^{78}$Kr, $^{80}$Kr, $^{82}$Kr, $^{83}$Kr, $^{84}$Kr, $^{88}$Kr; or $^{124}$Xe, $^{126}$Xe, $^{128}$Xe, $^{129}$Xe, $^{130}$Xe, $^{131}$Xe, $^{132}$Xe, $^{133}$Xe, $^{134}$Xe. However, preferably, the noble gas isotope whose abundances are measured can correspond to isotopes of different noble gases, such as $^{4}$He and $^{20}$Ne, $^{21}$Ne and $^{36}$Ar, $^{36}$Ar and $^{132}$Xe, $^{21}$Ne and $^{80}$Kr, $^{20}$Ne and $^{36}$Ar, $^{82}$Kr and $^{130}$Xe or $^{84}$Kr and $^{132}$Xe.

More preferably, the noble gas isotope whose abundance are measured comprise at least one of $^{78}$Kr, $^{88}$Kr, $^{82}$Kr, $^{83}$Kr, $^{84}$Kr, $^{88}$Kr, and $^{124}$Xe, $^{126}$Xe, $^{128}$Xe, $^{129}$Xe, $^{130}$Xe, $^{131}$Xe, $^{132}$Xe, $^{133}$Xe, $^{134}$Xe. Indeed, with such isotopes of noble gases, the accuracy of the determined hydrocarbon-water contact position can be improved.

As illustrated in FIG. 4, the invention also comprises a step of calculating 130 the hydrocarbon-water contact position in the hydrocarbon reservoir.

As described, this calculation is done from the measured abundances of isotopes of noble gases and from known sampling depth values of the at least two reservoir fluid samples.

This calculation can be done by any suitable means for establishing a correlation between the measured abundances and the known sampling depth values.

Firstly, the measured abundances values can be transformed in order to facilitate their interpretation. Hence, measured abundances values can be normalized, log transformed, square root transformed, or multiplicative inverse transformed.

Secondly, measured abundances values and known sampling depth values, transformed or not, can be used in a model to deduce the hydrocarbon-water contact position Mx1.

Figure 6:
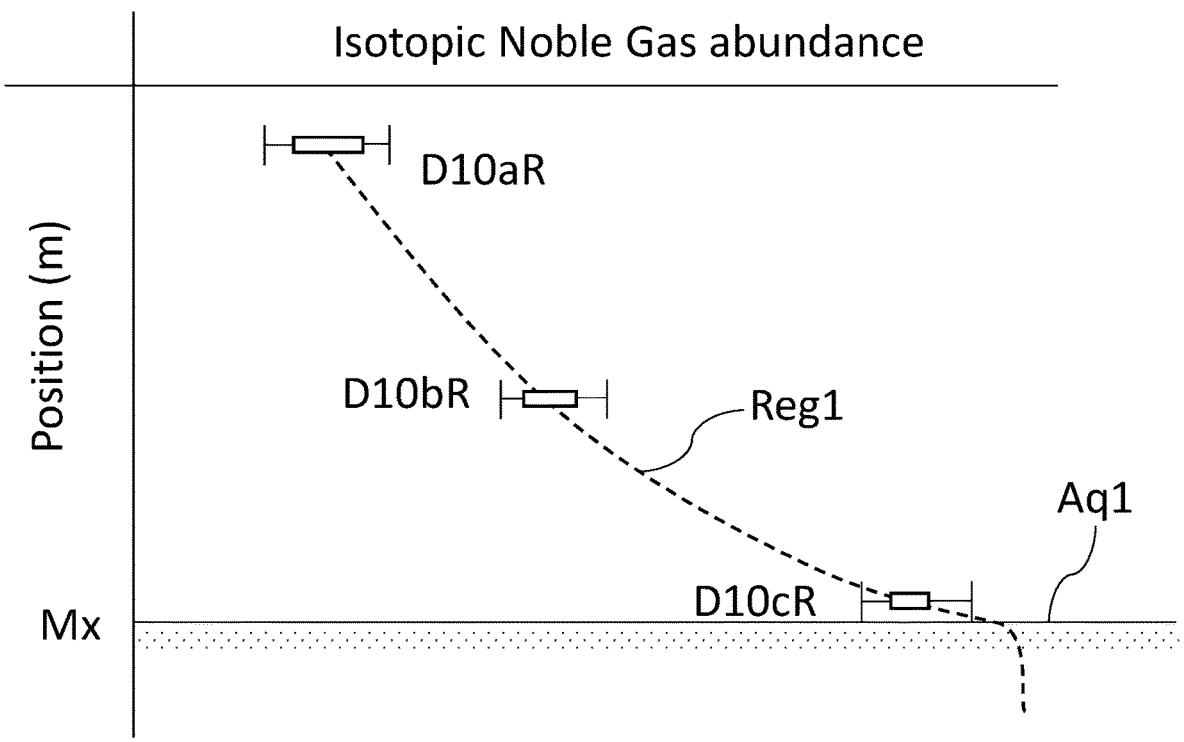
FIG. 6 is a representation of a graph showing plotted abundance values of isotopes of noble gas depending on the sample position (i.e. depth).

As illustrated in FIG. 6, the invention can comprise the use of a polynomial regression between measured abundances and known sampling depth values.

As illustrated in FIG. 6, isotopes noble gas abundances such as isotopes noble gas abundances box plot can be plotted D10$a$R, D10$b$R, D10$c$R with sampling depth and a polynomial regression Reg1 is added to the samples box plot. Where the regression line shows a stable value on the x-axis, there is an estimated depth of the contact between a hydrocarbon reservoir and the water in the aquifer Aq1 onto the y-axis.

As has been discussed, the method according to the invention does not require complex modeling and can be implemented only with the depth data and concentration values of noble gases.

However, in a method according to the invention, the step of calculating 130 the hydrocarbon-water contact position can comprise the use of additional data available for the studied hydrocarbon reservoir. Such data can comprise for example well log data and core data of the hydrocarbon reservoir. Preferably, measured concentrations and known sampling depth values and more particularly results of the calculation can be completed with other observed variables such as porosity, water saturation, and air permeability in function of depth.

Figure 7:
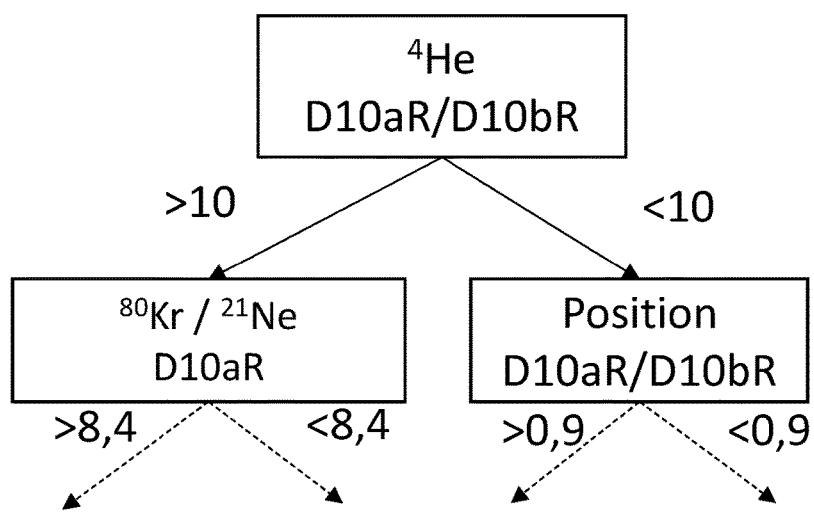
FIG. 7 is a representation of a part of a decision tree trained to determine the hydrocarbon-water contact position in hydrocarbon reservoir from abundance values of isotopes of noble gas depending on the sample position (i.e. depth).

Moreover, as illustrated in the FIG. 7, the method can also be used with a machine learning model trained on past data gathered from already studied reservoirs with known hydrocarbon-water contact position.

In that case, a method 100 for determining a hydrocarbon-water contact position in connected hydrocarbon reservoir(s), according to the invention can comprise a facultative step of collecting data from studied reservoirs with known hydrocarbon-water contact position. Such data are already available for multiple reservoirs with multiple configurations. Further, a method 100 for determining a hydrocarbon-water contact position according to the invention can comprise a step of training a prediction model, preferably a supervised learning model such as an ensemble prediction model.

Machine learning is now widely adopted in various industrial fields. Prediction models can be divided into unsupervised learning methods and supervised learning methods. The unsupervised learning methods make it possible to determine groups of observations without a priori. Hence, those groups will be formed without a need for a label value on input data. On the contrary, the supervised learning methods link an input to an output based on example input-output pairs.

Preferably, in the present invention, a machine learning technique is used to build a supervised prediction model configured to estimate hydrocarbon-water contact position from the measured abundances and the known sampling depth values of the at least two reservoir fluid samples. Among supervised learning methods, neural networks in particular deep learning, classification or regression trees, nearest neighbor search, and random forest are some of the most robust and efficient machine learning techniques according to the invention.

In the present invention, a supervised learning model in particular an ensemble prediction model that estimates hydrocarbon-water contact position from the measured abundances and the known sampling depth values of the at least two reservoir fluid samples, can be used. The training of said supervised learning model is preferably done with values of noble gas abundances, as input data, and with values of hydrocarbon-water contact position, as target data. These values used to train the supervised learning model can be considered as reference data. Preferably, a supervised learning model has been trained on several reservoirs.

Preferably, the use of a supervised learning model includes a method selected from: stacking, boosting, such as gradient boosting or adaptative boosting, and bagging such as random forest.

The method according to the invention can comprise a step of loading a supervised learning model. Preferably, the loaded supervised learning model has been trained according to the step of training describe above, more preferably with data collected according to the step of collecting data from studied reservoirs.

Back to the FIG. 7, a method 100 for determining a hydrocarbon-water contact position can comprise steps of calculating transformed data from the measured abundances and the known sampling depth values such as the ratio value of $^4$He from two samples, ratio value of two noble gas isotopes or ratio value of sampling depth values.

This illustration can correspond to the FIG. 2 arrangement where several sampling points have been done in each reservoir. Hence, the method can allow a simultaneous identification of three hydrocarbon-water contact position of disconnected reservoir.

A method according to the invention preferably comprise a step of determining, a median, an average, an upper estimate, and/or a lower estimate of hydrocarbon/water contact position for the studied hydrogen reservoir.

The present method of this invention is particularly adapted for use in the field of exploration and appraisal of reservoirs as it can prevent the drilling of several appraisal wells costing millions.

Hence, the invention can also relate to a method for determining location for an appraisal well, said method comprising a step of determining the hydrocarbon-water contact position in hydrocarbon reservoir according to a method of the invention.

As already stated, aspects of the present invention can be realized as a device, system, method or product of a computer program. Accordingly, the steps of the method according to the invention for determining a hydrocarbon-water contact position in a hydrocarbon reservoir described above can take the form of a computer program or a computer device.

According to another aspect, the invention relates to a non-transitory computer readable medium storing executable instructions which, when executed by a processor of a computer device, implement a method according to the invention or any of its embodiments.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such as wires, optical fibers, microwaves, radio waves, and other electromagnetic and/or optical carriers; and/or any combination of the foregoing.

In particular, the invention relates to a non-transitory computer readable medium storing executable instructions which, when executed by a processor, implement a method for determining a hydrocarbon-water contact position in a hydrocarbon reservoir, the method comprising calculating hydrocarbon-water contact position in a hydrocarbon reservoir, from measured concentrations values of at least one isotope of noble gas for each of the at least two reservoir fluid sample and known depth values of the at least two reservoir fluid samples. The measuring can be done for at least two isotopes of noble gases or more than two isotopes of noble gases, for example for at least three, preferably at least four isotopes of noble gases.

Preferably, the non-transitory computer readable medium, when executed by a processor, can implement a method for determining a hydrocarbon-water contact position in a hydrocarbon reservoir also comprising an acquisition of:

Measured abundance values of at least one isotope of noble gas from each of at least two reservoir fluid samples from the hydrocarbon reservoir, and Depth of collection values of the at least two reservoir fluid samples in the hydrocarbon reservoir.

Computer program code for performing operations for aspects of the present invention may be written in any combination of one or more programming languages, including an object-oriented programming language such as Java, C++, or similar, the programming language "C" or similar programming languages, a scripting language such as Perl, or similar languages, and/or functional languages such as Meta Language. Program code can run entirely on a user's computer, partly on a user's computer, and partly on a remote computer or entirely on the computer or remote server. In the latter scenario, the remote computer can be connected to a user's computer by any type of network, including a local area network (LAN) or a wide area network (WAN).

These computer program instructions may be stored on a computer readable medium that can direct a computing device (i.e. computer, server . . . ), so that the instructions stored in the computer readable medium produce a computing device configured to implement the invention.

According to another aspect, the invention relates to a computer device 300 for determining the hydrocarbon-water contact depth in hydrocarbon reservoir.

For purposes of this disclosure, a computer device 300 according to the invention may include any instrumentality or aggregate of instrumentalities operable to compute, classify, process, transmit, receive, retrieve, originate, store, display, detect, record, reproduce, handle, or utilize any form of information, intelligence, or data.

For example, a computer device 300 according to the invention may be a personal computer, a server, a network storage device, or any other suitable device and may vary in size, shape, performance, functionality, and price. The device 1 according to the invention may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

Figure 8:
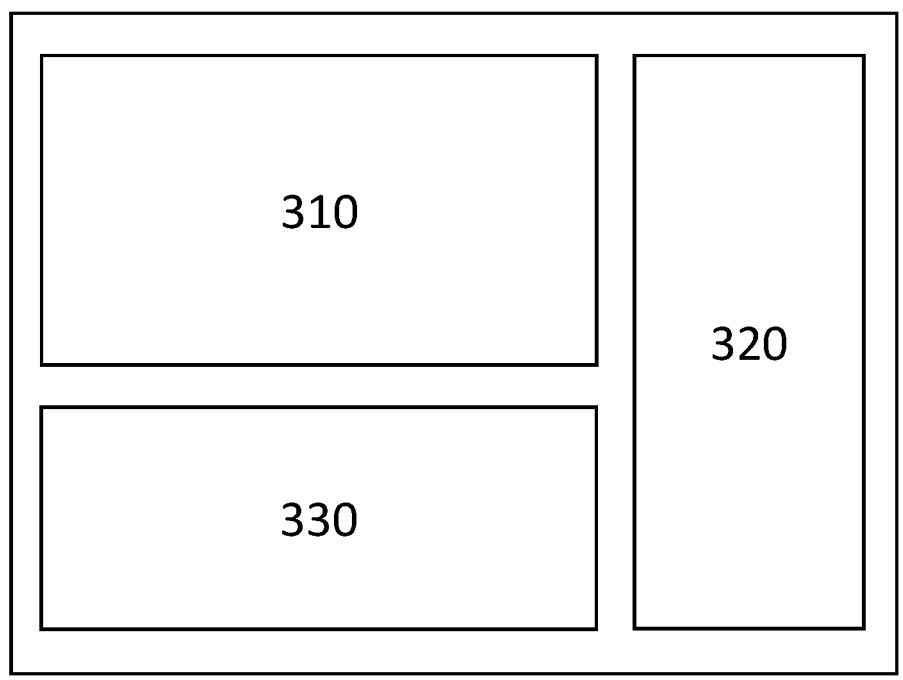
FIG. 8 is a representation of a computer device for determining the hydrocarbon-water contact position in hydrocarbon reservoir according to an embodiment of the invention.

In particular, as illustrated in FIG. 8, the computer device 300 may comprise: one or more memory component 310 configured to store depth and abundance values used for the hydrocarbon-water contact position determination, one or more communication interfaces 320 configured to acquired said depth and abundance values; and one or more processors 330 configured to process the said depth and abundance values to determine the hydrocarbon-water contact position in the hydrocarbon reservoir.

The memory component 310 may comprise any computer readable medium known in the art including, for example, a volatile memory, such as a static random access memory (SRAM) and a dynamic random access memory (DRAM), and/or a non-volatile memory, such as read-only memory, flash memories, hard disks, optical disks and magnetic tapes.

The memory component 310 may include a plurality of instructions or modules or applications for performing various functions. Thus, the memory component 310 can implement routines, programs, or matrix-type data structures. Preferably, the memory component 310 may comprise a medium readable by a computer system in the form of a volatile memory, such as a random-access memory (RAM) and/or a cache memory. The memory component 310, like the other modules, can for example be connected with the other components of the computer device 300 via a communication bus and one or more data carrier interfaces.

The memory component 310 can be configured to store all data and values related to the sampling depth of the at least two reservoir fluid samples in the hydrocarbon reservoir.

The memory component 310 can also be configured to store all data and values related to the measured abundance values of at least two isotopes of noble gas from each of at least two reservoir fluid samples from the hydrocarbon reservoir.

The memory component 310 can be configured to store abundance values of isotope of noble gas in known reservoirs or in aquifer in contact with the hydrocarbon reservoir.

Moreover, the memory component 310 is preferably configured to store instructions capable of implementing the method according to the invention.

The communication interface 320 is preferably configured to transmit data on at least one communication network and may implement a wired or wireless communication. The computer device 1 can communicate with other devices or computer systems and in particular with clients thanks to the communication interface 320. Preferably, the communication is operated via a wireless protocol such as Wi-Fi, 3G, 4G, and/or Bluetooth. These data exchanges may take the form of sending and receiving files. For example, the communication interface 320 may be configured to transmit a printable file. The communication interface may in particular be configured to allow the communication with a remote terminal, including a client. The client is generally any hardware and/or software capable of communication with the computer device 300.

A communication interface 320 according to the invention is, in particular, configured to acquire:
measured abundance values of at least one noble gas isotope from each of at least two reservoirs fluid samples from a hydrocarbon reservoir, and
sampling depth values of the at least two reservoirs fluid samples in the hydrocarbon reservoir.

In particular, the computer device 300 may include a communication interface 320 through which another computing system, such as a client, sends the measured abundance values of at least one isotope of noble gas of at least two reservoirs fluid samples from a hydrocarbon reservoir and sampling depth values of the at least two reservoirs fluid samples in the hydrocarbon reservoir.

Such computer device or client may all be located at the reservoir site, or considering the equipment required to measure isotopic abundance of the noble gases, at a location remote from the reservoir site.

The processor 330 may be operably coupled to the memory component 310 to execute instructions, encoded in programs, for carrying out the presently disclosed techniques, more particularly to perform the method according to the invention.

The encoded instructions may be stored in any suitable article of manufacture (such as the memory component 310) that includes at least one tangible non-transitory, computer-readable medium that at least collectively stores these instructions or routines. In this manner, the memory component 310 may contain a set of instructions that, when executed by the processor 330, performs one of the disclosed methods.

The memory component 310 may include any number of databases or similar storage media that can be queried from the processor 330 as needed to perform the disclosed methods.

In particular, the processor 330 is configured to calculate the hydrocarbon-water contact position in the hydrocarbon reservoir from the measured abundances of at least one isotope of noble gas, preferably at least two, from each of at least two reservoir fluid samples and known sampling depth values of the at least two reservoirs fluid samples.

These different modules or components are separated in FIG. 8, but the invention may provide various types of arrangement, for example a single module cumulating all the functions described here. Similarly, these modules or components may be divided into several electronic boards or gathered on a single electronic board.

A computer device 300 according to the invention can be incorporated into a computer system and able to communicate with one or several external devices such as a keyboard, a pointer device, a display, or any device allowing a user to interact with the computer device 300.

The computer device 300 may also be configured to communicate with or via a human-machine-interface. Thus, in one embodiment of the present invention, the device 1 can be coupled to a human machine interface (HMI). The HMI may be used to allow the transmission of parameters to the devices or conversely make available to the user the values of the data measured or calculated by the device.

In general, the HMI is communicatively coupled to a processor and includes a user output interface and a user input interface. The user output interface may include an audio and display output interface and various indicators such as visual indicators, audible indicators and haptic indicators.

The user input interface may include a keyboard, a mouse, or another navigation module such as a touch screen, a touchpad, a stylus input interface, and a microphone for inputting audible signals such as a user speech, data and commands that can be recognized by the processor.

The user interface may include various input/output devices that enable an operator to, for example, input values of measured abundance value of isotope of noble gas and depth of collection values.

EXAMPLE

Two sample were collected by a formation tester method at respectively 3487 meters depth and 3512 meters depth. After the transfer of the samples to surface, no evidence suggested a contamination from the drilling fluid.

Sub-sampling was done in laboratory conditions with pressure, temperature and volume controlled. C1-C5 analyses representative to the oil phase confirmed the absence of fractionation.

Noble gases isotopic abundances were measured by an isotope-ratio mass spectrometry coupled to a gas chromatography.

Treatment of the noble gas isotopic abundances values with a trained regression analysis base on isotope-ratio in those two samples indicate an estimated oil-water contact position comprise of 3518 m TVDss, which represents the TVD (for True Vertical Depth which is the measurement from the surface to the bottom of the exploration or the appraisal well, or anywhere along its length, in a straight perpendicular line) minus the elevation above mean sea level of a depth reference point of the well, whereas the confirmed oil-water contact position was positioned at 3523 m TVDss.

Hence a method according to the invention allow predictions of hydrocarbon-water contact position which are in good agreement with the drilled HWC.

Alternatively, a neural network or a random forest tree is trained with data from several reservoirs with input variables (mainly abundances of isotopes of noble gas, known sampling depth values) and target variable (hydrocarbon-water contact position). Machine learning models are used to determine patterns in the relationship between the input variables and the target variable. Then the trained supervised learning models are applied on each measured abundances of isotopes of noble gas and known sampling depth values to predict the hydrocarbon-water contact position.

The invention claimed is:

1. A method for determining a hydrocarbon-water contact position in connected hydrocarbon reservoir(s), said method comprising the steps of:
   Providing at least two reservoir fluid samples collected, from connected hydrocarbon reservoir(s), at different known sampling depth values,
   Measuring abundance of at least one isotope of noble gas from each of the at least two reservoir fluid samples, and
   Calculating the hydrocarbon-water contact position in the hydrocarbon reservoir(s) from the measured abundance(s) and the known sampling depth values of the at least two reservoir fluid samples.

2. The method according to claim 1, wherein the hydrocarbon-water contact position is an oil-water contact position or a gas-water contact position.

3. The method according to claim 1, wherein the at least two reservoir fluid samples are collected at known depth varying of at least ten meters.

4. The method according to claim 1, wherein the at least two reservoir fluid samples are collected from one same connected reservoir unit.

5. The method according to claim 1, wherein the at least two reservoir fluid samples are collected from several different connected reservoirs units.

6. The method according to claim 1, wherein the at least two reservoir fluid samples are collected in one or more wells from the same reservoir unit or connected reservoir units.

7. The method according to claim 1, wherein the at least two reservoir fluid samples are downhole samples.

8. The method according to claim 1, wherein said method is applied for several disconnected reservoirs and at least two reservoir fluid samples are provided for each disconnected reservoir.

9. The method according to claim 1, wherein the at least two reservoir fluid samples are collected by a formation tester or a drill stem test directly from the hydrocarbon reservoir(s) at reservoir pressure and temperature conditions.

10. The method according to claim 1, further comprising a step of collecting the at least two reservoir fluid samples by a formation tester at reservoir pressure and temperature conditions of the connected hydrocarbon reservoir(s).

11. The method according to claim 1, further comprising a step of bringing reservoir fluid samples to the surface and transferring them into PVT sampling bottles.

12. The method according to claim 1, further comprising a step of subsampling noble gas from the at least two reservoir fluid samples, the step of measuring abundance of at least one isotope of noble gas comprise the analysis of at least one noble gas isotope selected from: $^3$He, $^4$He, $^{20}$Ne, $^{21}$Ne, $^{22}$Ne, $^{36}$Ar, $^{38}$Ar, $^{40}$Ar, $^{78}$Kr, $^{80}$Kr, $^{82}$Kr, $^{83}$Kr, $^{84}$Kr, $^{88}$Kr, and $^{124}$Xe, 126Xe, 12sxe, 129xe, 13oxe, 131xe, 132xe, 133Xe, 134Xe.

13. The method according to claim 1, wherein the step of calculating hydrocarbon-water contact position from the measured abundances and known depth values of collection comprises the use of predetermined abundances values of isotopes of noble gases.

14. A computer device for determining a hydrocarbon-water contact position in a hydrocarbon reservoir, said computer device comprising:
   A communication interface configured to acquire:
      Measured abundance value of at least one isotope of noble gas from each of at least two reservoir fluid samples from the hydrocarbon reservoir, and
      Depth of collection values of the at least two reservoir fluid samples in the hydrocarbon reservoir;
   A processor configured to calculate hydrocarbon-water contact position in the hydrocarbon reservoir, from the measured abundance values and known depth values of the at least two reservoir fluid samples.

15. A non-transitory computer readable medium storing executable instructions which, when executed by a processor of a computer device, implements the method according to claim 1.

* * * * *